United States Patent [19]
Jean et al.

[11] Patent Number: 5,817,468
[45] Date of Patent: Oct. 6, 1998

[54] PROCESS FOR THE IDENTIFICATION OR IMMUNOASSAY OF POLYPEPTIDE ANTIGENS

[75] Inventors: Frédéric Jean; Gilles Kertesz; Béatrice Bourcier, all of Marseilles, France

[73] Assignee: Immunotech, Marseilles, France

[21] Appl. No.: 773,498

[22] Filed: Dec. 23, 1996

[30] Foreign Application Priority Data

Jan. 18, 1996 [FR] France .................................. 96 00894

[51] Int. Cl.$^6$ ........................ G01N 33/53; G01N 33/543; C07K 16/00
[52] U.S. Cl. ........................ 435/7.2; 435/7.1; 530/388.24; 530/389.2; 530/391.9; 436/518; 436/532
[58] Field of Search ................. 435/7.1, 7.2; 530/388.24, 530/389.2, 391.9; 436/518, 532

[56] References Cited

U.S. PATENT DOCUMENTS 4,415,546  11/1983  Ramachandran et al. .

FOREIGN PATENT DOCUMENTS 0 280 561  8/1988  European Pat. Off. .
1 505 400  3/1978  United Kingdom .
2 090 598  7/1982  United Kingdom .

OTHER PUBLICATIONS

Popper, H et al, Can Detect Prev., 10(3–4): 167–174, 1987 (Abst only).
Aillet, G. et al, Ann Pathol, 7(4–5): 325–9, 1987 (Abst only).
Houen, G. et al, J Immunol Meth, 181:187–200, 1995.
Nature, vol. 210, No. 5035, pp. 536–537 (30 Apr. 1966).
Lenard, J. et al., "Succinylation of gamma globulin."

*Primary Examiner*—Susan A. Loring
*Attorney, Agent, or Firm*—Browdy and Neimark

[57] ABSTRACT

Process for the identification or assay of a particular polypeptide antigen X in which an immunological determination of the presence of said polypeptide antigen X is carried out in a sample, characterized in that the sample is treated in vitro using at least one chemical reagent reacting on an epsilon -$NH_2$ function of a lysine residue or on a terminal alpha -$NH_2$ function of a peptide in order to carry out the linking of said reagent to said polypeptide antigen X and in this way to obtain a modified polypeptide antigen X, (polypeptide antigen Xm), the immunological determination of the presence of said polypeptide antigen X in said sample is then carried out using at least one antibody produced by immunization against a polypeptide antigen Y identical to the polypeptide antigen Xm or to an antigenic fragment of this antigen Xm.

29 Claims, No Drawings

PROCESS FOR THE IDENTIFICATION OR IMMUNOASSAY OF POLYPEPTIDE ANTIGENS

The present invention relates to a new process for the identification or immunoassay of polypeptide antigens.

FR-A-2 658 301 describes a process for the identification or assay of all the proteins bridged by dialdehydes originating from the oxidation in vivo of polyunsaturated fatty acids during cellular degeneration. This process uses a monoclonal antibody which is specific not for a particular protein, but is specific for the modification itself.

Among the peptide and protein antigens, certain may have a weakly immunogenic character. In other words, when they are injected into certain animals using standard immunization methods, it is rare to observe an antibody response against these antigens. For example, this is the case for the human peptide hormones ACTH (corticotropic hormone) and PTH (parathyroid hormone), when for example mice, rats or rabbits are immunized. The few antibodies directed against these molecules, having the required qualities for application in an immunoassay, were frequently obtained with great difficulty by immunization with the complete molecule or a fragment, linked to a carrier protein by the carbodiimide method or the glutaraldehyde method. These two examples are obviously not limitative, and numerous other soluble protein antigens, or membrane antigens at the cell surface, can also be considered as poorly immunogenic.

The weak immunogenicity depends both on the physicochemical properties of the antigen and on the characteristics of the immune system of the immunized animal. Two principle causes can lead to an absence of antibody response in an animal immunized with a peptide antigen. The first is poor stability of the molecule in vivo: the half-life of the antigen after injection into the animal will therefore be too short to stimulate an antibody response. The second is a "gap" in the antibody repertory of the immunized animal. This "gap" in the antibody repertory may be linked, in particular, to a high homology of structure between the protein immunogen and the corresponding endogenic protein of the immunized animal. This similarity will lead to the immune system not recognizing the immunogen as foreign to itself and therefore not producing antibodies in response to the injection of the peptide. Obviously, this is particularly true in the case where it is desired to immunize an animal with a protein which is completely identical with its own.

These two explanations can be illustrated by the case of human ACTH. The half-life of this hormone injected by intravenous route into a rat is of the order of 5 minutes; therefore it is a very unstable molecule. Of the 39 amino acids of which it is composed, only 3 residues are different between the human and murine proteins; therefore it is an antigen which is very well preserved between these two species. When it is injected into a mouse, this antigen therefore only rarely leads to the production of antibodies.

Despite their weakly immunogenic character, it would be desirable to have a process available which facilitates obtaining antibodies which can be used for example for the detection or assay of these antigens. This process would yield a much larger variety of antibodies, which would allow the development in particular of more effective systems for assay and detection than those which at present use the rare antibodies obtained by standard methods. In particular, in the case of the majority of immunoassays of human ACTH and PTH, the sensitivities required are only attained with very long incubation times (often more than 12 hours) and it would therefore be of interest to produce, using such a process, antibodies which allow much faster assays to be developed.

Furthermore, it has been shown above that the weakly immunogenic character of a peptide antigen could be linked to a poor stability in vivo. This poor stability may be expressed in vitro by a rapid degradation of the antigen in the sample to be assayed. This degradation may thus lead to an under estimation of the real concentration of the antigen. It would therefore be of great interest to have available a process which allows such antigens to be stabilized in order to facilitate the handling of samples and to avoid degradation.

This is why a subject of the present invention is a new process for the identification or assay of a particular polypeptide antigen X in which an immunological determination is carried out for the presence of said polypeptide antigen X in a sample, characterized in that the sample is treated in vitro using at least one reagent on an epsilon $-NH_2$ function of a lysine residue or
on an alpha $-NH_2$ function of a peptide, in order to carry out the linking of said reagent to said polypeptide antigen X and in this way to obtain a modified polypeptide antigen X, (polypeptide antigen Xm), the immunological determination of the presence of said polypeptide antigen X in said sample is then carried out using at least one antibody specific for said polypeptide antigen Xm and non-specific for the modification itself, produced by immunization against a polypeptide antigen Y identical with the polypeptide antigen Xm or an antigen fragment of this antigen Xm.

In other words, to produce and use antibodies for the immunological detection of peptide antigens which are weakly immunogenic, the Applicant has perfected a method the result of which is the modification of the structure of the antigen. The Applicant has discovered in a surprising fashion that this modification of the structure allows on the one hand the stimulation during immunizations of new cells which are capable of secreting antibodies against this modified antigen and thus to avoid the inability of the immunized animal to produce antibodies against the natural antigen and, on the other hand the stability of the antigen in certain cases to be improved, in particular by enhancing its resistance to proteolytic enzymes.

In fact, the absence of an antibody response in an immunized animal is not necessarily linked to a strict similarity between the polypeptide antigen and the endogenic protein of the animal, but more generally is linked to a genetic inability to produce antibodies against this antigen, or to a phenomenon of tolerance which will expressed by the suppression of this ability to produce these antibodies. The important point in the present process is therefore to modify the antigen in order to make it different and thus avoid this genetic inability or this suppression.

This method is based on a chemical modification of the natural polypeptide antigen X in order to obtain a polypeptide antigen Xm. A polypeptide antigen Y which is identical to the peptide antigen Xm, or corresponds to a fragment of this antigen will be used during the immunizations, insofar as this fragment corresponds to at least the size of an epitope (4 amino acids) of the antigen Xm and carries at least one chemically modified group.

The chemical modification of certain amino acids therefore induces a change in the structure of the polypeptide causing the appearance of different antigenic determinants and allows in certain cases the protection of or even the suppression of cleavage sites of proteolytic enzymes responsible for the degradation of the antigen in vivo and in the biological samples, in particular in cases where the modification occurs close to these sites.

Within the scope of the chemical modification of the biological sample before assay, the change in structure of certain proteolytic enzymes may lead to a loss of activity of these enzymes, which can also be expressed by an increase in the stability of the antigen in the modified sample.

Immunizations with the antigen Y therefore lead to the production of antibodies directed against the polypeptide antigen Xm, which are then used for example for assaying or detecting the antigen X in a sample which has undergone the same modification.

By "polypeptide antigen X" is meant a polypeptide constituted by at least 10 amino acids, preferably at least 25 amino acids, and by "fragment" of a polypeptide antigen is meant a peptide constituted by at least 4 amino acids and preferably less than 80% of the totality of the amino acids of the complete polypeptide antigen.

By "modified polypeptide antigen X" Xm is meant that a chemical modification reaction has been carried out on antigen X using one or more chemical reagents on one or more $-NH_2$ groups of one or more amino acids as defined above.

In order to modify these $-NH_2$ groups one or more specific reactive agents may be used.

The experimental conditions used may favor the modification either of the majority of the reactive $-NH_2$ groups or the modification of only one part of these groups, by adjusting in particular the quantities of reagents used, as known by a man skilled in the art.

The chemical modification of a reactive $-NH_2$ group of the antigen by coupling with the reactive agent used must be sufficiently small in order to obtain antibodies specific for the modified polypeptide antigen and not antibodies specific for the modification. Preferably, the coupled modifying group would have a molecular weight of less than 400 daltons and in particular less than 200 daltons. The specificity of the antibody for the antigen can be checked by verifying that the antibodies do not recognize other polypeptide antigens which have undergone the same modification.

In a preferred implementation of the process described above, the polypeptide antigen Y used in the immunizations to prepare antibodies can be obtained as follows:

The natural, complete, purified polypeptide antigen X or a fragment of this antigen is modified by the selected reagent or reagents.

Also, the polypeptide antigen Y can be synthetic or semi-synthetic. In particular, a polypeptide can be prepared by synthesis having the amino acid sequence of polypeptide X or of a fragment X and can be modified by subjecting it to the action of the reagent or reagents chosen.

The antigen Y is then injected directly or after coupling to a carrier protein into an animal for immunization and for obtaining monoclonal or polyclonal antibodies according to the methods known from the prior art. After prior modification of the sample by the selected reagent or reagents mentioned above, these antibodies will then be used according to the methods known from the prior art, to detect or assay the modified antigen.

In the case where the antibodies produced against antigen Y also recognize the non-modified natural antigen X with sufficient affinity, the assay or detection of the polypeptide antigen X can be carried out on non-modified samples.

The modification reagent can be advantageously chosen for its effectiveness (for modifying the $-NH_2$ groups carried by the antigen, it must also modify the numerous reactive $-NH_2$ groups carried by the other proteins present in the sample), for the rapidity of the modification reaction, for the simplicity of implementation of the reaction and for its compatibility with the realization of a subsequent immunoassay, and finally for its stability and its cheapness.

As reagents for the modification of the epsilon $-NH_2$ groups of the lysines and the alpha $-NH_2$ groups of the polypeptides acylation reagents such as carboxylic acid anhydrides such as succinic anhydride, acetic anhydride or citraconic anhydride, or activated esters such as derivatives of Nhydroxysuccinimidyl ester are preferably employed.

In particular, with succinic anhydride, the acylation reaction is rapid and effective (virtually all the reactive $-NH_2$ groups in the biological sample can be modified practically instantly); the number of charges carried by the protein is preserved since the $-NH_2$ groups are replaced by -COOH groups, which encourages high affinity antigen-antibody interactions.

As an example of an antigen, human ACTH or PTH, or their biologically-active fragments, for example the fragment 1-24 of ACTH, and in a general fashion any soluble or polypeptide membrane antigen containing reactive $-NH_2$ groups capable of being chemically modified may be cited. Of course, the process according to the invention is of particular interest for poorly immunogenic antigens.

A subject of the present invention is also the hybridomas obtained according to the standard methods of the prior art, by using the antigen Y defined above as antigen, said hybridomas allowing the production of monoclonal or polyclonal antibodies, and in particular a hybridoma producing anti-ACTH monoclonal antibodies acylated with succinic anhydride, chosen from the hybridomas deposited at the Collection Nationale de Culture de Microorganismes on 12th Dec., 1995 under the numbers I-1648, I-1649 and I-1650.

A subject of the present invention is also a monoclonal antibody produced by a hybridoma as defined above.

The sample can be for example a biological fluid, such as blood, serum, urine, sweat, tears etc. or also cell or tissue samples.

The above assay or detection method can use one or more monoclonal or polyclonal antibodies and can be for example: a radioimmunoassay by competition, or a radioimmunometric assay using a radioactive, luminescent, fluorescent or enzymatic tracer, or an immunoenzymometric assay. It can also be an immunoassay by particle agglutination. It can also be an immunohistochemical detection on a tissue sample or an analysis by flow cytometry of a cellular antigen, carried out on a cell suspension.

The following examples illustrate the present invention.

EXAMPLE 1

SYNTHESIS OF SUCCINYLATED ACTH

180 $\mu$l of succinic anhydride in solution at 3 mg/ml in dimethyl formamide is added to 1 mg of synthetic 1-39 ACTH in solution in 1 ml of 0.2M Hepes buffer, pH 8.2. After incubation for one hour at 20°–25° C., the reaction mixture is acidified by the addition of 4 ml of trifluoroacetic acid (TFA) at 1 % in water. The succinylated ACTH is then purified by reversed-phase high performance liquid chromatography (RP-HPLC), using a C18 micro-bondapack® column (Waters, USA) eluted with an acetonitrile gradient in a 0.05% TFA solution in water.

EXAMPLE 2

PREPARATION OF ACTH IMMUNOGENS

The succinylated ACTH is coupled on the one hand with bovine serum albumin (BSA) and on the other hand with porcine thyroglobulin (TG) by the carbodiimide method described by Goodfriend in Science 144, 1344 (1964). 1.25 mg of 1-ethyl-3-(3-dimethylaminopropyl) carbodiimide hydrochloride (EDC) in solution in 10 μl of water and 1.5 mg of BSA or TG in solution in 500 μl of a 0.1M Mes buffer (2-(N-morpholino) ethane sulphonic acid) pH 5.5 are added successively to 500 μg of succinylated ACTH in solution in 0.5 ml of water. After incubating for 4 hours at 20°–25° C., the immunogen is purified by size exclusion chromatography on a Superdex 200® 16/60 column (Pharmacia, Sweden) eluted with a 10 mM sodium phosphate, 150 mM NaCl buffer pH 7.2 (PBS) at a flow rate of 1 ml/minute.

EXAMPLE 3

IMMUNIZATION AND PRODUCTION OF ANTI ACTH MONOCLONAL ANTIBODIES

Balb/c mice receive monthly injections of 500 μl of emulsion at equal volumes of 25 μg of the immunogen obtained in Example 2 in solution in a phosphate buffer (PBS) with Freund's adjuvant. The first injection is carried out in complete adjuvant and the subsequent injections in incomplete adjuvant. Half of the volume is injected by intreperitoneal route and the other half by subcutaneous route. For each mouse, 3 to 4 immunizations with succinylated ACTH conjugated to BSA are followed by 4 to 5 immunizations with succinylated ACTH conjugated to TG. Serum samples are taken 10 days after each immunization, in order to monitor the level of anti-succinylated ACTH antibodies. Five days before removing their spleen, the animals selected to carry out a lymphocyte hybridization receive 50 μl by intravenous route and 100 μl by intraperitoneal route of a solution at 1 mg/ml of succinylated ACTH coupled with TG in PBS buffer. Three lymphocyte hybridizations with X63 AG3 myeloma cells carried out with three different animals, allowed to obtain 40 hybridomas secreting antisuccinylated ACTH monoclonal antibodies. Among these hybridomas, after screening the antibodies in the culture supernatants for their ability to recognise succinylated ACTH labelled with iodine 125, and succinylated ACTH immobilized in the wells of a microtitration plate, the hybridomas IMMU 148, IMMU 299 and IMMU 314 were selected and deposited at the Collection Nationale de Culture de Microorganismes Institut Pasteur, 28 rue du Dr Roux, 75724 in Paris CEDEX 15, France on 12th Dec., 1995, under the numbers I-1648, I1649 and I-1650, respectively.

The monoclonal antibodies used above are of the IgG1 isotype for IMMU 148 and of the IgA isotype for IMMU 299 and IMMU 314. Their dissociation constant for succinylated ACTH is $1.9 \times 10^{-10}$M, $1.3 \times 10^{-11}$M and $3.4 \times 10^{-10}$M able to bind simultaneously and without competition to succinylated ACTH. respectively. They have the property of being

EXAMPLE 4

MODIFICATION OF ACTH IN SOLUTION IN A PLASMATIC SAMPLE AND IN AN ACTH STANDARD

250 μl of plasmatic sample are dispensed in tubes containing 6.15 mg of succinic anhydride and 4 mg of lyophilized phenol red. 125 μl of an alkaline solution composed of 0.42 M KOH and 0.166 M of $KH_2PO_4$ at pH 6.7 are then distributed into each tube. The succinylation reaction is almost instantaneous and is expressed by the modification of the dye reagent from the colour red to the colour yellow.

The operation is carried out in a similar fashion with standard solutions containing known quantities of ACTH.

EXAMPLE 5

ASSAY OF MODIFIED ACTH

After treatment by succinic anhydride as described above, 300 μl of plasma sample or standard solution containing a known quantity of ACTH in human serum, are dispensed in tubes covered with two anti-modified ACTH monoclonal antibodies, IMMU 148 and IMMU 314 which are able to bind simultaneously to succinylated ACTH. The tubes are then incubated for 1 hour at 20°–25° C. with constant shaking. After removing its contents by suction, each tube is washed with 2 ml of a solution of NaCl at 9 g/l in water containing 0.005% Tween 20. 100 μl of a solution containing 250,000 cpm of a third monoclonal antibody IMMU 299 labelled with iodine 125, capable then to bind to succinylated ACTH simultaneously with the two others, in a PBS buffer containing 0.1% BSA, were distributed in each tube. After incubation for 3 hours at 20°–25° C. with constant shaking, the tubes are again emptied of their contents by suction and washed with 2 ml of the washing solution. The radioactivity bound to each tube which is proportional to the quantity of ACTH in the sample, is measured with a gamma counter for 1 minute. The concentration of each sample is calculated by plotting the measurement of the radioactivity on the standard curve drawn using the standard ACTH solutions.

This assay has the same sensitivity as the best available commercial kits, but it is carried out in 4 hours whereas the existing kits require incubation for 20 hours.

EXAMPLE 6

STABILITY OF SUCCINYLATED ACTH

Calibrated solutions of ACTH in human serum were assayed according to the protocol above. One part of these solutions is then modified with succinic anhydride, then stored for 24 hours at 20°–25° C. and finally assayed according to the protocol above; the other part is directly stored at 20°–25° C. for 24 hours, then modified with succinic anhydride and finally assayed according to the same protocol. The results of these assays show that, after storage for 24 hours at 20°–25° C., approximately 61% of modified ACTH is found and only 2.7% of native ACTH. The modification of the ACTH in solution in serum by succinic anhydride therefore leads to an increase in the stability of the molecule.

A man skilled in the art will appreciate that it is also possible to treat a sample with a reagent on a -COOH function of an aspartic or glutamic acid residue or on a terminal -COOH function of a peptide, or also on an -SH function of a cysteine residue in order to carry out the linking of said reagent to said polypeptide antigen X and thus to obtain a modified polypeptide antigen X (polypeptide antigen Xm). Among the reagents of modification, the following can therefore be mentioned: the alkylation reagents of -SH groups carried by the cysteines such as the corresponding haloacetates and amides such as iodoacetate, bromoacetate, chloroacetate, iodoacetamides, bromoacetamide and chloroacetamide or such as the maleimide derivatives such as N-ethylmaleimide and finally the carbodiimides such as (1 ethyl 3 dimethylaminopropyl) carbodiimide (EDC) combined with an appropriate nucleophilic compounds, such as glycinamide, which allow the modification of the -COOH groups of glutamic and aspartic acids and the terminal -COOH groups of polypeptides.

One or more chemical modification reagents can therefore also be used to modify two or more of the two types of reactive group.

We claim:

1. Process for the identification or assay of a particular polypeptide antigen X in which an immunological determination is carried out for the presence of said polypeptide antigen X in a sample, characterized in that the sample is treated in vitro using at least one modifying reagent on an epsilon -$NH_2$ function of a lysine residue or on an alpha -$NH_2$ function of a peptide, in order to carry out the linking of said modifying agent to said polypeptide antigen X as a chemical modifying group and in this way to obtain a modified polypeptide antigen X, (polypeptide antigen Xm), wherein the chemical modifying group has a molecular weight less than 400 daltons and the immunological determination of the presence of said polypeptide antigen X in said sample is then carried out using at least one antibody specific for said polypeptide antigen Xm and non-specific for the modification itself, produced by immunization against a polypeptide antigen Y identical to the polypeptide antigen Xm or to an antigenic fragment of this antigen Xm.

2. Process according to claim 1 characterized in that a polypeptide antigen Y identical to the complete polypeptide antigen Xm is used to carry out the immunizations.

3. Process according to claim 1 characterized in that a polypeptide antigen Y corresponding to a fragment of the polypeptide antigen Xm is used to carry out the immunization and in this way to obtain antibodies directed against a particular region of the antigen Xm.

4. Process according to claim 1 characterized in that a single reagent for modification is used.

5. Process according to one of claim 1 characterized in that several reagents for modification are used.

6. Process according to claim 5 characterized in that the reagent or reagents are selected from: succinic anhydride, acetic anhydride, derivatives of the esters of N-hydroxy succinimide.

7. Process according to claim 1 characterized in that the sample is a biological fluid such as blood, serum, urine, sweat or tears.

8. Process according to claim 7 characterized in that the polypeptide antigen X is human corticotropic hormone (ACTH).

9. Process according to claim 7 characterized in that the polypeptide antigen is human parathyroid hormone (PTH).

10. Process according to claim 9 characterized in that the assay method is an immunoassay by competition or a radioimmunometric assay using a radioactive, luminescent, fluorescent or enzymatic tracer, or an immunoassay by particle agglutination, said method using one or more monoclonal or polyclonal antibodies.

11. Process according to claim 6 characterized in that the sample is a tissue sample and the polypeptide antigen X is detected by an immunohistochemical method.

12. Process according to claim 6 characterized in that the sample is a cellular suspension and where the polypeptide antigen X is detected by a flow cytometry method.

13. A hybridoma producing antiacylated ACTH with succinic anhydride monoclonal antibodies, selected from the group consisting of hybridomas deposited at the Collection Nationale de Culture de Microorganismes on 12th Dec., 1995 under the accession numbers I-1648, I-1649 and I-1650.

14. An anti-acylated ACTH monoclonal antibody produced by a hybridoma as defined in claim 13.

15. Process according to claim 1 characterized in that the polypeptide antigen X is human corticotropic hormone (ACTH).

16. Process according to claim 1 characterized in that the polypeptide antigen is human parathyoid hormone (PTH).

17. Process according to claim 1 characterized in that the assay method is an immunoassay by competition or a radioimmunometric assay using a radioactive, luminescent, fluorescent or enzymatic tracer, or an immunoassay by particle agglutination, said method using one or more monoclonal or polyclonal antibodies.

18. Process according to claim 1 characterized in that the sample is a tissue sample and the polypeptide antigen X is detected by an immunohistochemical method.

19. Process according to claim 1 characterized in that the sample is a cellular suspension and where the polypeptide antigen X is detected by a flow cytometry method.

20. A process for the identification or assay of a particular polypeptide antigen X in which an immunological determination is carried out for the presence of said polypeptide antigen X in a sample, characterized in that the sample is treated in vitro using at least one modifying reagent on an epsilon -$NH_2$ function of a lysine residue or on an alpha -NH2 function of a peptide, in order to carry out the linking of said modifying agent to said polypeptide antigen X as a chemical modifying group and in this way to obtain a modified polypeptide antigen X, designated polypeptide Xm, wherein the chemical modifying group has a molecular weight less than 400 daltons and the immunological determination of the presence of said polypeptide antigen X in said sample is then carried out using at least one antibody specific for said polypeptide antigen Xm and non-specific for the modification itself, produced by immunization against a polypeptide antigen Y coupled to a carrier protein via a coupling reagent, wherein said polypeptide antigen Y is identical to the polypeptide antigen Xm or to an antigenic fragment of polypeptide antigen Xm.

21. Process according to claim 20, wherein the assay is selected from the group consisting of an immunoassay by competition, a radioimmunometric assay using a radioactive, luminescent, fluorescent or enzymatic tracer, and an immunoassay by particle agglutination, said assay using one or more monoclonal or polyclonal antibodies.

22. Process according to claim 20 characterized in that a single reagent for modification is used.

23. Process according to claim 20 characterized in that several reagents for modification are used.

24. Process according to claim 23 characterized in that the reagent or reagents are selected from: succinic anhydride, acetic anhydride, derivatives of the esters of N-hydroxy succinimide.

25. Process according to claim 20 characterized in that the sample is a biological fluid such as blood, serum, urine, sweat or tears.

26. Process according to claim 20 characterized in that the polypeptide antigen X is human corticotropic hormone (ACTH).

27. Process according to claim 20 characterized in that the polypeptide antigen is human parathyoid hormone (PTH).

28. Process according to claim 20 characterized in that the sample is a tissue sample and the polypeptide antigen X is detected by an immunohistochemical method.

29. Process according to claim 20 characterized in that the sample is a cellular suspension and where the polypeptide antigen X is detected by a flow cytometry method.

* * * * *